United States Patent [19]

Hefner, Jr.

[11] Patent Number: 4,506,063

[45] Date of Patent: Mar. 19, 1985

[54] ADVANCED EPOXY RESINS CONTAINING TRIAZINE OR BOTH TRIAZINE AND OXAZOLINE GROUPS

[75] Inventor: Robert E. Hefner, Jr., Lake Jackson, Tex.

[73] Assignee: The Dow Chemical Company, Midland, Mich.

[21] Appl. No.: 582,415

[22] Filed: Feb. 22, 1984

[51] Int. Cl.$^3$ .................. C08G 59/00; C08G 65/00
[52] U.S. Cl. ........................... 528/96; 528/89; 528/93; 528/98; 528/99; 528/104
[58] Field of Search ............ 528/98, 99, 104, 89, 528/93, 96

[56] References Cited

U.S. PATENT DOCUMENTS

| | | | |
|---|---|---|---|
| 2,506,486 | 5/1950 | Bender et al. | 260/47 |
| 2,741,607 | 4/1956 | Bradley et al. | 260/248 |
| 2,809,942 | 10/1957 | Cooke, Jr. | 260/2 |
| 2,810,706 | 10/1957 | Frazier et al. | 260/45.5 |
| 2,864,805 | 12/1958 | Cooke, Jr. | 260/47 |
| 2,971,942 | 2/1961 | Masters et al. | 260/2 |
| 3,334,110 | 8/1967 | Schramm | 528/96 |
| 3,413,377 | 11/1968 | Schramm et al. | 528/96 |
| 3,477,990 | 11/1969 | Dante | 528/98 |
| 3,766,296 | 10/1973 | Kassner | 528/96 |

FOREIGN PATENT DOCUMENTS 56-26925  3/1981  Japan .

*Primary Examiner*—John Kight
*Assistant Examiner*—Garnette D. Draper
*Attorney, Agent, or Firm*—J. G. Carter

[57] ABSTRACT

Advanced epoxy resins are prepared which contain triazine groups or both triazine and oxazoline groups. When cured, these resins have higher heat distortion temperatures and/or higher elongation values than advanced epoxy resins which do not contain triazine groups or triazine and oxazoline groups.

20 Claims, No Drawings

ADVANCED EPOXY RESINS CONTAINING TRIAZINE OR BOTH TRIAZINE AND OXAZOLINE GROUPS

BACKGROUND OF THE INVENTION

The present invention provides novel advanced epoxy resin compositions containing triazine or both triazine and oxazoline groups, as well as cured compositions prepared from said epoxy resins.

Epoxy resins are the reaction product of a diphenol or polyphenol with an epihalohydrin and a basic-acting material. Said reaction generally involves two distinct steps: coupling reaction of the epihalohydrin and diphenol or polyphenol to provide a halohydrin intermediate and dehydrohalogenation reaction of the halohydrin intermediate to provide the glycidyl ether product.

It is known, for example, as taught by Bender et al. in U.S. Pat. No. 2,506,486 that epoxy resins can be reacted with diphenols. Said reaction involves etherification of hydroxyl groups via reaction with epoxide groups. This reaction is designated as an advancement reaction and the product thereof is an advanced epoxy resin.

Preparation of polyepoxides containing triazine groups is taught by R. E. Hefner, Jr. in Application Ser. No. 547,537 filed Oct. 3, 1983. The process disclosed therein uses an easily prepared mixed cyanate of a diphenol or polyphenol. More specifically, the process disclosed comprises reacting at least one material having an average of more than one aromatic hydroxyl group per molecule with at least 0.01 but not more than 0.95 moles of cyanogen halide or mixture of cyanogen halides per aromatic hydroxyl group in the presence of a suitable base in a quantity of from about 0.01 to about 1.1 moles per aromatic hydroxyl group at a temperature and time sufficient to essentially complete the reaction and thereafter recovering the resultant cyanate mixture; trimerizing the resultant cyanate mixture in the presence of a suitable trimerization catalyst at a temperature and time to essentially complete the trimerization reaction; epoxidizing the resultant trimerized product in a conventional manner by reaction with an epihalohydrin with subsequent dehydrohalogenation with a basic-acting material and finally recovering the resultant triazine functional glycidyl ether product. Excellent control over the molecular weight and content of triazone groups is provided by this process. The resultant epoxy resin compositions possess unusually high thermal stability as well as excellent overall physical and mechanical properties.

Preparation of polyepoxides containing triazine and oxazoline groups is taught by R.E.Hefner, Jr. in patent application Ser. No. 576304 filed 2/2/84. The process disclosed therein uses the aforementioned mixed cyanate of a diphenol or polyphenol. Co-oligomerization of this cyanate mixture with an epoxy resin, such as a diglycidyl either of bisphenol A, provides hydroxyaromatic oligomers both triazine and oxazoline groups. Oligomers prepared from co-oligomerization of the mixed cyanate of a diphenol with an epoxy resin using mole ratios of epoxy groups to nitrile groups of about 1 to 10 about 1 to 40 or more are disclosed for the process described. The oligomers, and unreacted diphenol, if any, are then epoxidized using methods well known in the art. The resultant epoxy resin compositions posses excellent thermal stability as well as enhanced mechanical properties.

The advanced epoxy resin compositions of the present invention contain triazine groups or both triazine and oxazoline groups and are derived by reaction of the respective triazine-containing or triazine-containing and oxazoline-containing hydroxyaromatic oligomers with an epoxy resin. The invention consists of the advanced epoxy resins as well as cured compositions thereof.

SUMMARY OF THE INVENTION

The present invention pertains to advanced epoxy resin compositions containing triazone groups or both triazine and oxazoline groups prepared
(1) by reacting
   (a) at least one hydroxyaromatic oligomer containing at least one triazine group, or
   (b) at least one hydroxyaromatic oligomer containing both at least one triazine group and at least one oxazoline group, or
   (c) a mixture of (a) and (b) with
(2) at least one material having an average of more than one 1,2-epoxy group per molecule wherein the components are employed in proportions which provide a ratio of hydroxyl groups to epoxy groups of from about 0.1:1 to about 1:1, preferably from about 0.1:1 to about 0.5:1.

Another aspect of the present invention pertains to the product resulting from curing the aforementioned advanced epoxy resins with a curing quantity of a suitable curing agent and/or catalyst or mixture of curing agents and/or catalysts.

DETAILED DESCRIPTION OF THE INVENTION

Suitable materials having an average of more than one aromatic hydroxyl group per molecule which can be employed to prepare the cyanate mixture precursor to the triazine functional oligomers or the triazine and oxazoline functional oligomers include, for example, those represented by the formulas:

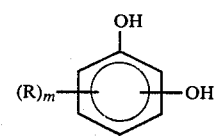

I.

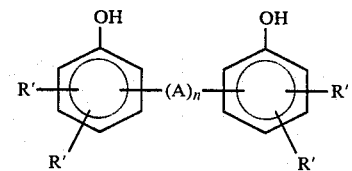

II.

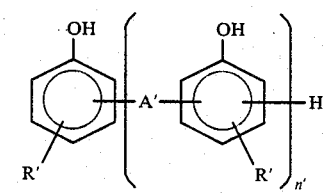

III.

wherein A is a divalent hydrocarbon group having from 1 to about 12, preferably from about 1 to about 6 carbon atoms,

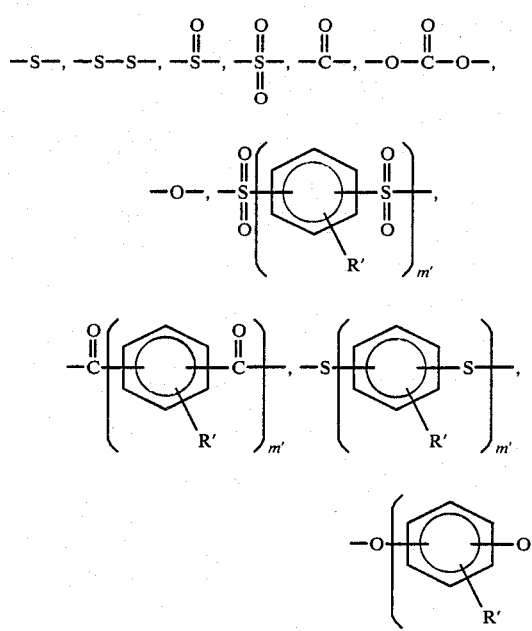

and the like; each A' is a divalent hydrocarbon group having from 1 to about 3, preferably 1, carbon atoms; each R is independently hydrogen, halogen, preferably chlorine or bromine, a hydrocarbyl group having from 1 to about 6 carbon atoms or a hydroxyl group; each R' is independently hydrogen or a hydrocarbyl group having from 1 about 6 carbon atoms or a halogen, preferably chlorine or bromine; m has a value from zero to about 2; m' has a value from 1 to about 100, preferaby from 1 to about 10; n has a value of zero or 1 and n' has a value from about 1.01 to about 6.

Particularly suitable aromatic hydroxyl-containing compounds include, for example, o-, m- and p-dihydroxybenzene, 2-tert butyl hydroquinone, 2,4-dimethyl resorcinol, 2,5-di-tert butyl hydroquinone, tetramethyl hydroquinone, 2,4,6-trimethyl resorcinol, 4-chlororesorcinol, 4-tert butyl pyrocatechol, 1,1-bis(4-hydroxyphenyl) ethane; 2,2-bis(4-hydroxyphenyl)propane; 2,2-bis(4-hydroxyphenyl)- pentane; bis(4,4'-dihydroxyphenyl)methane; 4,4'-dihydroxydiphenyl, 2,2'-dihydroxydiphenyl, 3,3',5,5'-tetramethyl- 4,4'-dihydroxydiphenyl, 3,3',5,5'-tetrachloro-4,4'-dihydroxydiphenyl, 3,3',5,5'-tetrachloro-2,2'-dihydroxydiphenyl, 2,2',6,6'-tetrachloro-4,4'-dihydroxydiphenyl, 4,4'-bis((3-hydroxy)phenoxy)-diphenyl, 4,4'-bis((4-hydroxy) phenoxy)-diphenyl, 2,2'-dihydroxy-1,1'-binaphthyl, and other dihydroxydiphenyls; 4,4'-dihydroxydiphenyl ether, 3,3',5,5'-tetramethyl-4,4'-dihydroxydiphenyl ether, 3,3',5,5'-tetrachloro-4,4'-hydroxydiphenyl ether, 4,4'-bis(p-hydroxyphenoxy)-diphenyl ether, 4,4'-bis(p-hydroxyphenyl isopropyl)-diphenyl ether, 4,4'-bis(p-hydroxyphenoxy)-benzene, 4,4'-bis(p-hydroxyphenoxy) -diphenyl ether, 4,4'-bis(4(4-hydroxyphenoxy)- phenyl sulfone)-diphenyl ether, and other dihydroxydiphenyl ethers; 4,4'-dihydroxydiphenyl sulfone, 3,3',- 5,5'-tetramethyl-4,4'-dihydroxydiphenyl sulfone, 3,3'5,5'- tetrachloro-4,4'-dihydroxydiphenyl sulfone, 4,4'-bis(p-hydroxyphenyl isopropyl)-diphenyl sulfone, 4,4'-bis((4-hydroxy)-phenoxy)-diphenyl sulfone, 4,4'-bis((3-hydroxy)- phenoxy)-diphenyl sulfone, 4,4'-bis(4-(4-hydroxyphenyl- isopropyl)-phenoxy)-diphenyl sulfone, 4,4'-bis(4(4-hydroxy) diphenoxy)-diphenyl sulfone, and other diphenyl sulfones; 4,4'-dihydroxydiphenyl methane, 4,4'-bis(p- hydroxyphenyl)-diphenyl methane, 2,2'-bis(p-hydroxyphenyl) propane, 3,3',5,5'-tetramethyl-2,2'-bis(p-hydroxyphenyl) propane, 3,3',5,5'-tetrachloro-2,2'-bis(p-hydroxyphenyl) propane, 1,1-bis(p-hydroxyphenyl)-cyclohexane, bis-(2- hydroxy-1-naphthyl)-methane, 1,2-bis(p-hydroxyphenyl)- 1,1,2,2-tetramethyl ethane, 4,4'-dihydroxybenzophenone, 4,4'-bis(4-hydroxy)phenoxy-benzophenone, 1,4-bis(p- hydroxyphenyl isopropyl)-benzene, phloroglucinol, pyrogallol, 2,2',5,5'-tetrahydroxy-diphenyl sulfone, other dihydroxydiphenyl alkanes, mixtures thereof and the like.

Suitable cyanogen halides which can be employed to prepare the cyanate mixture precursor include, for example, cyanogen chloride, cyanogen bromide, mixtures thereof and the like.

If desired, the method reported in Organic Synthesis, Vol. 61, page 35–37 (1983), published by John Wiley & Sons, may be used to generate the required amount of cyanogen halide in situ, although this is less preferred than using neat cyanogen halide.

Suitable base materials which can be employed to prepare the cyanate mixture precursor include both inorganic bases and tertiary amines, such as, for example, sodium hydroxide, potassium hydroxide, triethylamine, pyridine, lutidine, mixtures thereof and the like. The tertiary amines are most preferred as the base material.

Suitable trimerization catalysts which can be employed for conversion of the cyanate mixture to triazine functional oligomers include, for example, metal salts of carboxylic acids, such as, for example, lead octoate, zinc stearate, zinc acetylacetonate, at concentrations of about 0.001 to 5 percent. Most preferred catalysts are cobalt naphthenate and cobalt octoate, mixtures thereof and the like. The aforementioned catalysts are also employed for co-oligomerization of the cyanate mixture with an epoxy resin to provide oligomers containing both triazine and oxazoline groups.

Suitable epoxy resins for co-oligomerization with the cyanate mixture are those represented by the following formulas:

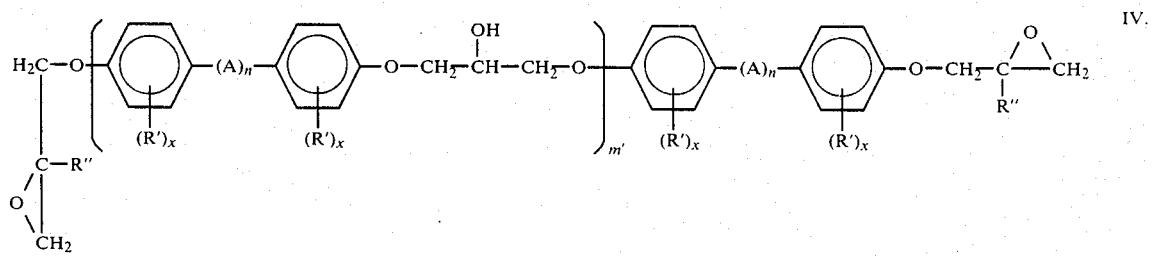

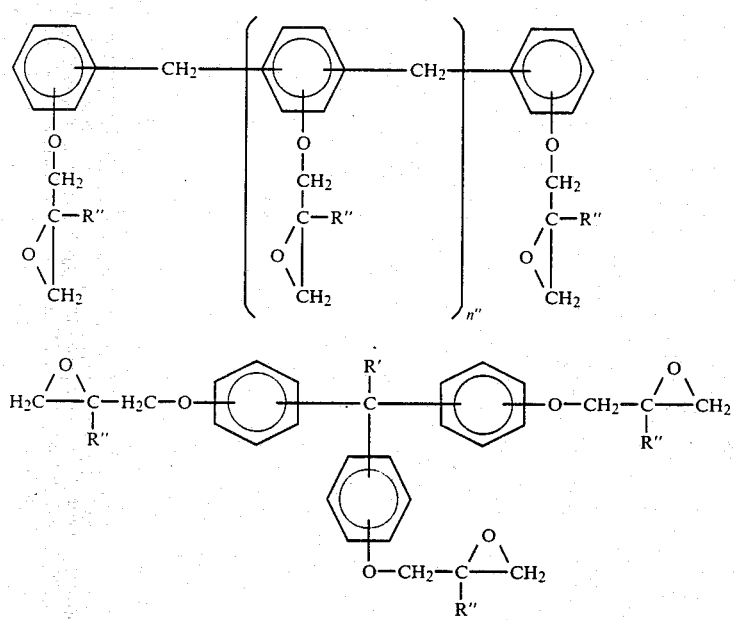

wherein A, R', m' and n are as herein before defined, R" is independently hydrogen or a hydrocarbyl group having from 1 to about 3 carbon atoms, x has a value of from 0 to about 4 and n" has a value of from 0 to about 100, preferably from 0 to about 5.

Although the co-oligomerization of the cyanate mixture with an epoxy resin provides both triazine and oxazoline functionality in the oligomer product, it is felt that other reactions may also be occurring. Unreacted phenolic groups may copolymerize with a portion of the epoxide groups of the epoxy resin during the co-oligomerization reaction. Unreacted phenolic groups may react with cyanate groups to form iminocarbonate linkages which may in turn react with remaining epoxide groups.

Reaction to provide the cyanate mixture is usually conducted at a temperature of from about -40° C. to about 60° C., preferably from about -20° C. to about 25° C. for from about 10 minutes (600 s) to about 120 minutes (7200 s), preferably from about 10 minutes (600 s) to about 60 minutes (3600 s).

If desired, the reaction to provide the cyanate mixture can be conductd in the presence of an inert solvent reaction medium. Suitable such solvents include, for example, water, chlorinated hydrocarbons, ketones, mixtures thereof and the like.

The trimerization or co-oligomerization reactions are both usually conducted at a temperature of from about 70° C. to about 250° C., preferably from about 70° C. to about 200° C. for a period of from about 15 minutes (900 s) to about 120 minutes (7200 s), preferably from about 30 minutes (1800 s) to about 75 minutes (4500 s). These reactions are preferably performed in the presence of the aforementioned catalyst(s).

Suitable epoxy resins for advancement reaction with the hydroxyaromatic oligomers containing triazine group(s) or triazine and oxazoline groups are represented by Formulas IV, V and VI above. The advancement reaction is optionally, although preferably, performed in the presence of 0.01 to 2.0 percent by weight of a suitable catalyst. Suitable catalysts include bases, basic acting materials, acids and the like.

Preferred catalysts are the quarternary ammonium salts and phosphonium salts. A most preferred catalyst is benzyltrimethylammonium chloride. Reaction times and temperatures vary depending on the composition of the epoxy resin reactant used; the amount and type of catalyst used, if any; the presence of inert solvent, if any. Typically, the advancement reaction when catalyzed is conducted at a temperature of from about 50° C. to about 150° C., preferably from about 90° C. to about 120° C. for from about 15 minutes (900 s) to about 240 minutes (14400 s), preferably from about 30 minutes (1800 s) to about 90 minutes (5400 s). Advancement reaction times and temperatures are generally longer and higher, respectively, for the non-catalyzed reaction.

Suitable curing agents and/or catalysts for curing and/or preparing epoxy resins are described in the Handbook of Epoxy Resins by Lee and Neville, McGraw-Hill, (1967), as well as U.S. Pat. Nos. 3,477,990, 3,948,855 and 4,366,295 which are incorporated herein by reference.

The cured advanced epoxy resins of this invention possess improvements in one or more physical or mechanical properties such as tensile strength, flexural strength, percent elongation and/or heat distortion temperature. Furthermore, the invention allows for incorporation of triazine or both triazine and oxazoline groups into an epoxy resin without having to epoxidize (i.e., react with an epihalohydrin followed by dehydrohalogenation) the hydroxy aromatic oligomers containing triazine or triazine oxazoline groups.

The epoxy resins of the present invention can be used to prepare castings, coatings, laminates, encapsulations and the like, and are especially suited for use in applications requiring high mechanical strength.

The following examples are illustrative of the invention, but are not to be construed as to limiting the scope thereof in any manner.

EXAMPLE 1

A. Preparation of Diphenol Cyanate Mixture

Cyanogen bromide (1.10 mole, 116.52 grams) was added to a reactor containing a stirred solution of bisphenol A (2.00 moles, 456.60 grams) in acetone (1050 milliliters) cooled to −5° C. under a nitrogen atmosphere. The stirred solution was allowed to equilibrate at −5° C. Triethylamine (1.00 mole, 101.19 grams) was then added to the reactor over a 17 minute (1020 s) period so as to maintain the reaction temperature at −2° to −5° C. After completion of the triethylamine addition, the reactor was maintained at −2° to 5° C. for an additional 30 minutes (1800 s), followed by addition of the reaction product to chilled water (1.5 gallons, 5.7 liters) with agitation. After 5 minutes (300 s), the water and product mixture was subjected to multiple extractions with three 800 milliliter portions of methylene chloride. The combined methylene chloride extracts were sequentially washed with 500 milliliters of dilute 5% aqueous hydrochloric acid, 1000 milliliters of water and then dried over anhydrous sodium sulfate. The dry methylene chloride extract was filtered and solvent removed by rotary evaporation under vacuum. The diphenol cyanate mixture was recovered (416.0 grams) as a light yellow colored solid at room temperature (25° C.). Infrared spectrophotometric analysis demonstrated the presence of the nitrile groups as well as unreacted hydroxyl groups. Liquid chromatographic analysis demonstrated the presence of 56.00 area percent bisphenol A, 34.89 area percent bisphenol A monocyanate, and 9.11 area percent bisphenol A dicyanate.

B. Trimerization of Diphenol Cyanate Mixture

A portion of the diphenol cyanate mixture (415.0 grams) from A above and 6.0 percent cobalt naphthenate (0.10 percent by weight, 0.42 gram) were thoroughly mixed and placed in a glass tray. The tray was then placed in a forced-air, convection-type oven and maintained for 1.25 hours (4500 s) at 177° C. The hydroxyaromatic oligomers containing triazine groups were recovered in quantitative yield as a transparent, brittle solid at room temperature (25° C.). The oligomers had a greenish-colored cast due to the catalyst. At the 177° C. temperature, the oligomers were totally fluid. Infrared spectrophotometric analysis demonstrated complete disappearance of the nitrile groups, appearance of the triazine groups, and the presence of unreacted hydroxyl groups.

C. Epoxy Resin Advancement with Hydroxyaromatic Oligomers Containing Triazine Groups A portion (15.92 grams, 0.10 hydroxyl equivalent) of the hydroxyaromatic oligomers containing triazine groups from B above, a diglycidyl ether of bisphenol A (219.60 grams, 1.2 equiv.) having an epoxide equivalent weight (EEW) of 183 and 60 percent aqueous benzyltrimethylammonium chloride (0.236 gram) catalyst were added to a reactor and heated to 120° C. with stirring under a nitrogen atmosphere. After 60 minutes (3600 s) at the 120° C. reaction temperature, the reactor was cooled and the epoxy resin advanced with oligomers containing triazine groups was recovered as a transparent, light yellow colored liquid. Epoxide titration revealed the resin to contain 18.28 percent epoxide (235.23 EEW).

D. Curing of Epoxy Resin Advanced with Hydroxyaromatic Oligomers Containing Triazine Groups A portion (230.31 grams, 0.9791 epoxide equivalent) of the epoxy resin advanced with hydroxyaromatic oligomers containing triazine groups from C above was heated to 75° C. and blended with methylenedianiline (48.47 grams, 0.2448 mole) which also was heated to 75° C. This mixture was used to prepare a clear, unfilled ⅛ inch (0.3175 cm) casting for heat distortion temperature (264 psi, 1820 kPa), tensile and flexural strength, flexural modulus, percent elongation and average Barcol Hardness (934-1 scale) determinations. The casting was cured at 75° C. for 2.0 hours (7200 s), followed by post curing at 125° C. for 2.0 hours (7200 s), 175° C. for 2.0 hours (7200 s), then 200° C. for 2.0 hours (7200 s). Mechanical properties of tensile (8) and flexural (6) test pieces were determined using an Instron machine with standard test methods (ASTM D-638 and D-790). Heat distortion temperature of clear casting test pieces (2) was determined using an Aminco Plastic Deflection Test (American Instrument Co.) with standard test methods (ASTM D-648 modified). The results are given in Table I.

EXAMPLE 2

A. Epoxy Resin Advancement with Hydroxyaromatic Oligomers Containing Triazine Groups A portion (31.84 grams, 0.20 hydroxyl equiv.) of the hydroxyaromatic oligomers containing triazine groups from Example 1-B, a diglycidyl ether of bisphenol A (219.60 grams, 1.2 equiv.) having an EEW of 183 and 60 percent aqueous benzyltrimethylammonium chloride (0.251 gram) catalyst were added to a reactor and heated to 120° C. with stirring under a nitrogen atmosphere. After 60 minutes (3600 s) at the 120° C. reaction temperature, the reactor was cooled and the epoxy resin advanced with oligomers containing triazine groups was recovered as a transparent yellow colored liquid. Epoxide titration revealed the resin to contain 15.38 percent epoxide (279.58 EEW).

B. Curing of Epoxy Resin Advanced with Hydroxyaromatic Oligomers Containing Triazine Groups A portion (241.13 grams, 0.8374 epoxide equiv.) of the epoxy resin advanced with hydroxyaromatic oligomers containing triazine groups from A above was heated to 100° C. and blended with methylenedianiline (41.45 grams, 0.2093 mole) which also was heated to 100° C. This mixture was used to prepare a clear, unfilled casting using the method of Example 1-D. Mechanical properties were evaluated using the method of Example 1-D. The results are given in Table I.

EXAMPLE 3

A. Preparation of Diphenol Cyanate Mixture

Cyanogen bromide (1.10 mole, 116.52 grams) was added to a reactor containing a stirred solution of bisphenol A (2.00 moles, 456.60 grams) in acetone (1050 milliliters) cooled to −5° C. under a nitrogen atmosphere. The stirred solution was allowed to equilibrate at −5° C. Triethylamine (1.00 mole, 101.19 grams) was added to the reactor over an 18 minute (1080 s) period so as to maintain the reaction temperature at 0° to −5° C. After completion of the triethylamine addition, the reactor was maintained at 0° to 5° C. for an additional 30 minutes (1800 s) followed by addition of the reaction product to chilled water (1.5 gallons, 5.71 l) with agitation. After 5 minutes (300 s), the water and product mixture was subjected to multiple extractions with three 800 milliliter portions of methylene chloride. The combined methylene chloride extracts were sequentially washed with 500 milliliters of dilute hydrochloric acid (5 percent aqueous), 1000 milliliters of water and then dried over anhydrous sodium sulfate. The dry methylene chloride extract was filtered and solvent removed by rotary evaporation under vacuum. The resultant diphenol cyanate mixture was recovered (398.0 grams) as a light yellow colored solid at room temperature (25° C.) Infrared spectrophotometric analysis demonstrated the presence of the nitrile groups as well as unreacted hydroxyl groups. Liquid chromatographic analysis demonstrated the presence of 57.11 area percent bisphenol A, 35.33 area percent bisphenol A monocyanate, and 7.56 area percent bisphenol A dicyanate.

B. Co-oligomerization of Diphenol Cyanate Mixture and an Epoxy Resin

A portion of the diphenol cyanate mixture (388.7 grams) from A above, an epoxy resin (25.64 grams), and 6.0 percent cobalt naphthenate (0.10 percent by weight, 0.41 gram) were thoroughly mixed and placed in a glass tray. The epoxy resin had an epoxide equivalent weight (EEW) of 340.4 and was prepared by reaction of a diglycidyl ether of bisphenol A (EEW=183, 0.8 equiv., 146.4 grams) with bisphenol A (0.4 equiv., 45.66 grams) and benzyltrimethylammonium chloride catalyst (60 percent aqueous, 0.19 gram) at 120° C. for 50 minutes (3000 s). The tray was then placed in a forced-air, convection-type oven and maintained for 1.25 hours (4500 s) at 177° C. The hydroxyaromatic co-oligomerization product containing triazine and oxazoline groups was recovered in quantitative yield as a transparent, light amber-colored, brittle solid at room temperature (25° C.). Infrared spectrophotometric analysis demostrated complete disappearance of the nitrile groups, appearance of the triazine groups, appearance of the oxazoline groups and the presence of unreacted hydroxyl groups.

C. Epoxy Resin Advancement with Hydroxyaromatic Oligomers Containing Triazine and Oxazoline Groups A portion (16.62 grams, 0.10 hydroxyl equiv.) of the hydroxyaromatic oligomers containing triazine and oxazoline groups from B above, a diglycidyl ether of bisphenol A (219.60 grams, 1.2 equiv.) having an EEW of 183 and 60 percent aqueous benzyltrimethylammonium chloride (0.236 gram) catalyst were added to a reactor and heated to 120° C. with stirring under a nitrogen atmosphere. After 60 minutes (3600 s) at the 120° C. reaction temperature, the reactor was cooled and the epoxy resin advanced with oligomers containing triazine and oxazoline groups was recovered as a transparent light yellow colored liquid. Epoxide titration revealed to resin to contain 18.28 percent epoxide (235.23 EEW).

D. Curing of Epoxy Resin Advanced with Hydroxyaromatic Oligomers Containing Triazine and Oxazoline Groups A portion (231.64 grams, 0.9847 epoxide equiv.) of the epoxy resin advanced with hydroxyaromatic oligomers containing triazine and oxazoline groups from C above was heated to 75° C. and blended with methylenedianiline (48.75 grams, 0.2462 mole) which was also heated to 75° C. This mixture was used to prepare a clear, unfilled casting using the method of Example 1-D. Mechanical properties were evaluated using the method of Example 1-D. The results are given in Table I.

EXAMPLE 4

A. Epoxy Resin Advancement with Hydroxyaromatic Oligomers Containing Triazine and Oxazoline Groups A portion (33.24 grams, 0.20 hydroxyl equiv.) of the hydroxyaromatic oligomers containing triazine and oxazoline groups from Example 3-B, a diglycidyl ether of bisphenol A (219.60 grams, 1.2 equiv.) having an EEW of 183 and 60 percent aqueous benzyltrimethylammonium chloride (0.253 gram) catalyst were added to a reactor and heated to 120° C. with stirring under a nitrogen atmosphere. After 60 minutes (3600 s) at the 120° C. reaction temperature, the reactor was cooled and the epoxy resin advanced with oligomers containing triazine and oxazoline groups was recovered as a transparent yellow colored liquid. Epoxide titration revealed the resin to contain 15.32 percent epoxide (280.68 EEW).

B. Curing of Epoxy Resin Advanced with Hydroxyaromatic Oligomers Containing Triazine and Oxazoline Groups A portion (238.64 grams, 0.8502 epoxide equiv.) of the epoxy resin advanced with hydroxyaromatic oligomers containing triazine and oxazoline groups from A above was heated to 100° C. and blended with methylenedianiline (42.09 grams, 0.2126 mole) which was also heated to 100° C. This mixture was used to prepare a clear, unfilled casting using the method of Example 1-D. Mechanical properties were evaluated using the method of Example 1-D. The results are given in Table I.

COMPARATIVE EXPERIMENT A

A. Preparation of Advanced Epoxy Resin Free of Triazine and Oxazoline Groups A diglycidyl ether of bisphenol A (292.80 grams, 1.6 equiv.) having an EEW of 183 was reacted with bisphenol A (30.44 grams, 0.2666 equiv.) to provide an advanced epoxy resin. The diglycidyl ether of bisphenol A, bisphenol A and 60 percent aqueous benzyltrimethylammonium chloride (0.32 gram) catayst were added to a reactor and heated to 120° C. with stirring under a nitrogen atmosphere. After 60 minutes (3600 s) at the 120° C. reaction temperature, the reactor was cooled and the epoxy resin advanced with bisphenol A was recovered as a transparent, light yellow colored liquid. Epoxide titration revealed the resin to contain 17.04 percent epoxide (252.35 EEW).

B. Curing of the Advanced Epoxy Resin Free of Triazine and Oxazoline Groups

A portion (250.0 grams, 0.9907 epoxide equiv.) of the epoxy resin advanced with bisphenol A from A above was heated to 75° C. and blended with methylenedianiline (49.04 grams, 0.2477 mole) which was also heated to 75° C. This mixture was used to prepare a clear, unfilled casting using the method of Example 1-D. Mechanical properties were evaluated using the method of Example 1-D. The results are given in Table I.

EXAMPLE 5

A. Epoxy Resin Advancement with Hydroxyaromatic Oligomers Containing Triazine Groups A portion (46.42 grams, 0.30 hydroxyl equiv.) of hydroxyaromatic oligomers containing triazine groups prepared in the manner of Example 1-A and 1-B, a diglycidyl ether of bisphenol A (219.60 grams, 1.2 equiv.) having an EEW of 183 and 60 percent aqueous benzyltrimethylammonium chloride (0.27 gram) catalyst were added to a reactor and heated to 120° C. with stirring under a nitrogen atmosphere. After 60 minutes (3600 s) at the 120° C. reaction temperature, the reactor was cooled and the epoxy resin advanced with oligomers containing triazine groups was recovered as a transparent yellow colored solid. Epoxide titration revealed the resin to contain 12.73 percent epoxide groups (337.78 EEW).

B. Curing of Epoxy Resin Advanced with Hydroxyaromatic Oligomers Containing Triazine Groups A portion (252.60 grams, 0.7478 epoxide equiv.) of the epoxy resin advanced with hydroxyaromatic oligomers containing triazine groups from A above was heated to 100° C. and blended with methylendianiline (37.02 grams, 0.1870 mole) which was also heated to 100° C. This mixture was used to prepare a clear, unfilled casting using the method of Example 1-D. Mechanical properties were evaluated using the method of Example 1-D. The results are given in Table I.

TABLE 1

|  | Example 1 | Example 2 | Example 3 | Example 4 | Example 5 | Comparative Experiment A |
|---|---|---|---|---|---|---|
| Barcol Hardness | 40 | 38 | 38 | 40 | 31 | 38 |
| Heat Distortion Temp. (°C./°F.) | 149.5/301.1 | 147.5/297.5 | 149.0/298.4 | 146/294.8 | 143/289 | 139.5/283.1 |
| Tensile Strength, psi | 11,333 | 11,829 | 10,842 | 10,498 | 11,037 | 11,269 |
| Tensile Strength =, kPa | 78,139 | 81,559 | 74,753 | 72,382 | 76,098 | 77,698 |
| Elongation, % | 4.13 | 5.69 | 4.18 | 4.30 | 4.94 | 3.51 |
| Flexural Strength, psi | 19,786 | 21,415 | 20,435 | 21,680 | 21,083 | 19,734 |
| Flexural Strength =, kPa | 137,041 | 147,652 | 140,895 | 149,479 | 145,363 | 136,062 |
| Flexural Modulus, psi | 411,000 | 421,000 | 413,000 | 409,000 | 376,000 | 420,000 |
| Flexural Modulus =, MPa | 2832 | 2901 | 2846 | 2818 | 2591 | 2894 |

I claim:

1. Advanced epoxy resin compositions containing triazine groups or triazine and oxazoline groups which are prepared by a method which comprises reacting (A) (1) at least one hydroxyaromatic oligomer containing at least one triazine group or (2) at least one hydroxyaromatic oligomer containing at least one triazine group and at least one oxazoline group or (3) a mixture of (1) and (2) with (B) at least one material having an average of more than one 1,2-epoxy group per molecule and wherein the components are present in quantities which provide a ratio of phenolic hydroxyl groups to epoxy groups of from about 0.1:1 to about 1:1.

2. An epoxy resin composition of claim 1 wherein said epoxy groups of component B are glycidyl ether groups and the components are reacted in quantities which provide a ratio of phenolic hydroxyl groups to epoxy groups of from about 0.1:1 to about 0.5:1.

3. An epoxy resin composition of claim 1 wherein said component (B) is a diglycidyl ether of a compound containing a plurality of phenolic hydroxyl groups.

4. An epoxy resin composition of claim 3 wherein component (B) is a glycidyl ether represented by formulas (IV), (V) or (VI) or a mixture of such glycidyl ethers

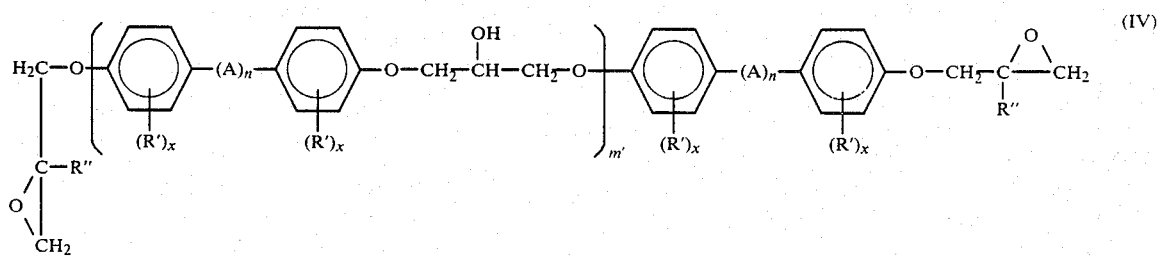

(IV)

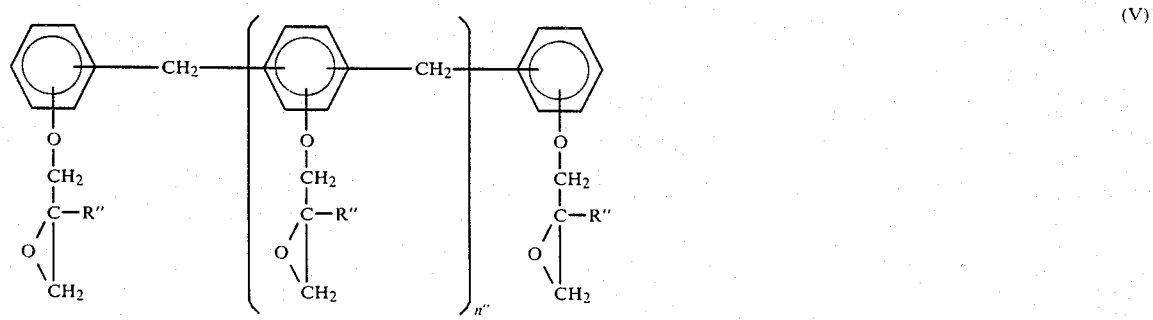

(V)

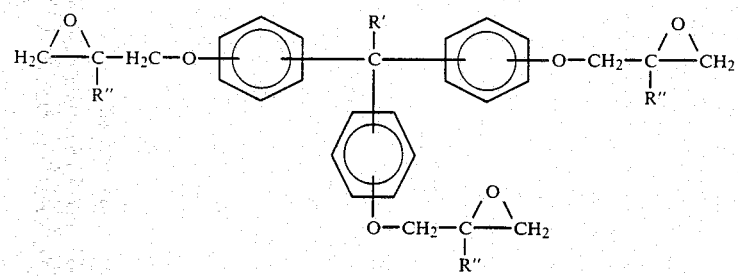

wherein R″ is independently hydrogen or a hydrocarbyl group having from 1 to about 3 carbon atoms; R′ is independently hydrogen or a hydrocarbyl group having from 1 to about 6 carbon atoms or a halogen; x has a value of from 0 to about 4; m′ and n″ have a value from 1 to about 100; n has a value of zero or 1; and A is a divalent hydrocarbon group having from 1 to about 12 carbon atoms,

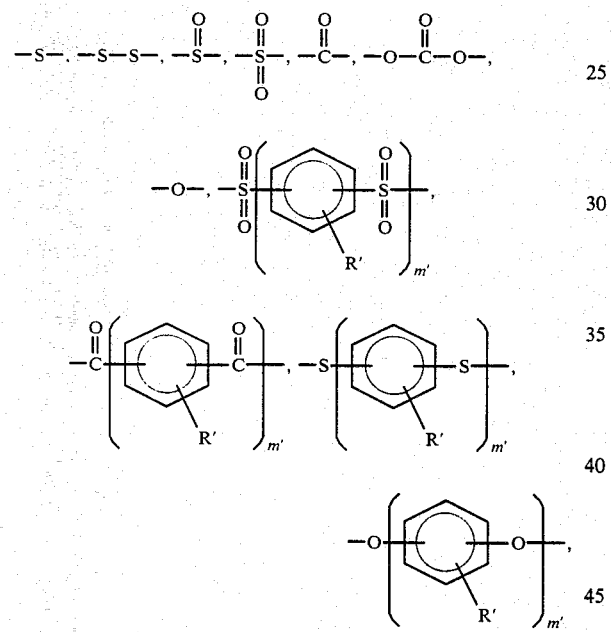

5. An epoxy resin composition of claim 4 wherein component (B) is a diglycidyl ether of bisphenol A.

6. An epoxy resin composition of claims 1, 2, 3, 4 or 5 wherein
(i) component (A-1), if present, is prepared by trimerizing in the presence of a suitable trimerization catalyst the product resulting from reacting a material having an average of more than one aromatic hydroxyl group per molecule with from about 0.01 but not more than about 0.95 moles of a cyanogen halide per aromatic hydroxy group in the presence of a suitable base in a quantity of from about 0.01 to about 1.1 moles per aromatic hydroxyl group and
(ii) component (A-2), if present, is prepared by co-oligomerizing in the presence of a suitable catalyst at least one material containing at least one 1,2-epoxy group per molecule and the product resulting from reacting a material having an average of more than one aromatic hydroxyl group per molecule with from about 0.01 but not more than about 0.95 moles of a cyanogen halide per aromatic hydroxy group in the presence of a suitable base in a quantity of from about 0.01 to about 1.1 moles per aromatic hydroxyl group.

7. An epoxy resin composition of claim 6 wherein
(i) said material containing an average of more than one phenolic hydroxyl group per molecule as mentioned in components (A-1) and (A-2) is selected from that represented by formulas I, II or III or mixtures thereof;

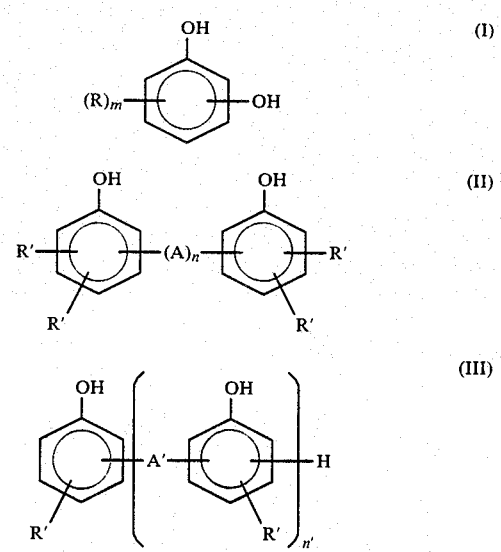

wherein R is independently hydrogen, halogen, a hydrocarbyl group having from 1 to about 6 carbon atoms or a hydroxyl group; A is a divalent hydrocarbon group having from 1 to about 3; and R′, A′, n,n′ and m′ are herein before defined;
(ii) said material having an average of more than one 1,2-epoxy group per molecule as mentioned in component (A-2) is represented by formulas (IV), (V), or (VI) as defined in claim 4 or mixture thereof; and
(iii) the cyanogen halide is employed in a quantity which provides from about 0.05 to about 0.55 moles of cyanogen halide per aromatic hydroxyl group.

8. An epoxy resin composition of claim 7 wherein
(i) any epoxy resin employed is a diglycidyl ether of bisphenol A and
(ii) any cyanogen halide employed is cyanogen chloride.

9. A product resulting from curing an epoxy resin composition of claims 2, 3, 4 or 5 in the presence of a curing amount of a suitable curing agent or catalyst or combination thereof.

10. A product of claim 6 in the presence of a curing amount of a suitable curing agent or catalyst or combination thereof.

11. A product of claim 7 in the presence of a curing amount of a suitable curing agent or catalyst or combination thereof.

12. A product of claim 8 in the presence of a curing amount of a suitable curing agent or catalyst or combination thereof.

13. A product of claim 9 wherein said curing agent or catalyst or combination thereof is an aromatic amine.

14. A product of claim 13 wherein said aromatic amine is methylenedianiline.

15. A product of claim 10 wherein said curing agent or catalyst is an aromatic amine.

16. A product of claim 15 wherein said aromatic amine is methylenedianiline.

17. A product of claim 11 wherein said curing agent or catalyst is an aromatic amine.

18. A product of claim 17 wherein said aromatic amine is methylenedianiline.

19. A product of claim 12 wherein said curing agent or catalyst is an aromatic amine.

20. A product of claim 19 wherein said aromatic amine is methylenedianiline.

* * * * *